(12) United States Patent
Harston et al.

(10) Patent No.: US 6,747,178 B1
(45) Date of Patent: Jun. 8, 2004

(54) METHOD OF PERFORMING A CHEMICAL REACTION

(75) Inventors: Paul Harston, Preston (GB); Malcolm John Atherton, Preston (GB); Robert G. Holmes, Idaho Falls, ID (US); Richard Dickinson Chambers, Durham (GB); Robert Spink, Durham (GB)

(73) Assignee: British Nuclear Fuels plc, Cheshire (GB)

( * ) Notice: Subject to any disclaimer, the term of this patent is extended or adjusted under 35 U.S.C. 154(b) by 0 days.

(21) Appl. No.: 09/530,231

(22) PCT Filed: Nov. 5, 1998

(86) PCT No.: PCT/GB98/03285

§ 371 (c)(1), (2), (4) Date: Oct. 2, 2000

(87) PCT Pub. No.: WO99/22857

PCT Pub. Date: May 14, 1999

(30) Foreign Application Priority Data

Nov. 5, 1997 (GB) .............................................. 9723260

(51) Int. Cl.[7] .............................................. C07C 17/00
(52) U.S. Cl. ...................................................... 570/175
(58) Field of Search ......................................... 570/175

(56) References Cited

FOREIGN PATENT DOCUMENTS

| WO | WO 96/12540 | | 5/1996 |
|---|---|---|---|
| WO | WO 96/12541 | * | 5/1996 |
| WO | WO 97/00442 | | 1/1997 |
| WO | WO 97/14497 | | 4/1997 |

* cited by examiner

*Primary Examiner*—Deborah D. Carr
(74) *Attorney, Agent, or Firm*—Myers, Bigel, Sibley & Sajovec

(57) ABSTRACT

According to the present invention there is provided a method of carrying out a chemical reaction between at least two fluids, the method comprising providing respective flow paths for the at least two fluids, said flow paths communicating with each other in a region in which the at least two fluids may contact each other, and flowing the at least two fluids along said flow paths such that in said region the at least two fluids contact each other and a chemical reaction occurs between them, said region having a width perpendicular to the direction of flow in the range 10–10,000 micrometers. It has been found that using a so-called "microreactor", that is a reactor having dimensions perpendicular to the flow direction of less than 10,000 micrometers, according to the present method, improved control over a fluid chemical reaction can be achieved, which can result in significant improvements in reaction product yield and/or purity, as well as other benefits. The present method has been found to be particularly beneficial for fluorination reactions.

24 Claims, 4 Drawing Sheets

Equation 1

Equation 2

Equation 3

Equation 1

Equation 2

Equation 3

Equation 4

Equation 5

METHOD OF PERFORMING A CHEMICAL REACTION

This application is a 371 of PCT/GB98/03285 filed Nov. 5, 1998.

The present invention relates to a method of carrying out a chemical reaction, in particular a fluorination reaction between at least two fluids.

A constant aim in the chemical industry and chemistry generally is to improve control over chemical reactions. Greater control over reactions may lead to, for example, improvements in safety, increases in the reaction product yield and/or purity, or the isolation of valuable highly reactive intermediate products. In particular, greater control over reagent mixing, fluid flow, heat sinking/sourcing and catalytic efficiency is desirable. A general method which provides such improved control over reactions would therefore be advantageous.

According to the present invention there is provided a method of carrying out a fluorination reaction between at least two fluids, one of the at least two fluids comprising a compound to be fluorinated and another of the at least two fluids comprising a fluorinating agent, the method comprising providing respective flow paths for the at least two fluids, said flow paths communicating with each other in a region in which the at least two fluids may contact each other, and flowing the at least two fluids along said flow paths such that in said region the at least two fluids contact each other and a chemical reaction occurs between them, said region having a width perpendicular to the direction of flow in the range 10–10,000 micrometers.

It has been found that using a so-called "microreactor", that is a reactor having dimensions perpendicular to the flow direction of less than 10,000 micrometers, according to the present method, improved control over a fluid chemical reaction can be achieved, which can result in significant improvements in reaction product yield and/or purity, as well as other benefits.

The reaction region may have a width (defined as perpendicular to the direction of flow) in the range 10–10,000 micrometers. Preferably, the reaction region has a width in the range 10–500 micrometers. Most preferably, the reaction region has a width in the range 10–200 micrometers.

The length of the reaction region (measured in the direction of the flow) is typically in the range 10 micrometer to 1 meter. The optimum length will be determined by the kinetics of the reaction to be carried out and the flow rates to be employed. For example, a reaction having slow kinetics would require a longer reactor length than a reaction with faster kinetics for the same flow rate.

Typically, the microreactor used in the present method is the same general type of apparatus as disclosed in patent applications WO 96/12541 and WO 96/12540, and the teaching of those documents is incorporated herein by reference. Input and output ports for reactants and products respectively may be arranged to suit the particular reaction being carried out. Examples of different microreactor configurations are shown in FIGS. 1 to 5.

Whereas the apparatus as described in WO 96/12541 and WO 96/12540 is formed from silicon or glass, the microreactor used in the present invention may be produced in a number of materials using standard processing techniques. For example, in fluorination reactions, the microreactor may be formed from nickel, copper or zirconium or another suitable material non-reactive with fluorine. Polymer materials may be used to form the microreactor for some reactions.

An advantage of the method of the present invention is that reactions may be readily scaled up from laboratory scale to operating plant scale. The reaction conditions are identical and the technology is immediately transferable.

Figure 1:
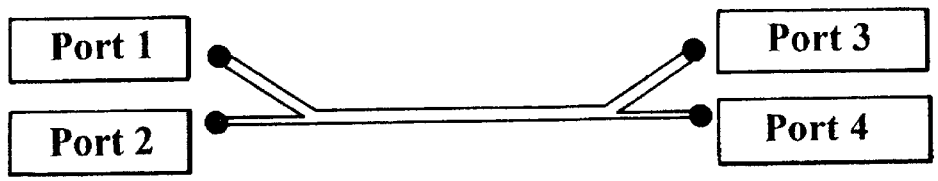
FIGS. 1–5 illustrate examples of different micro-reactor configurations.

The reactions may be any of liquid-liquid, liquid-gas, or gas-gas type reactions or may involve a supercritical fluid. The fluids may, or may not, be miscible with each other.

The region where the flow paths communicate with each other may include essentially the whole of the flow paths of one of the fluids. One of the fluids may substantially surround the or another of said fluids transversely to the direction of fluid flow.

A fluorination reaction may be carried out by a method of the invention using a multiplicity of flow paths thereby forming a multiplicity of regions in which the chemical reaction occurs.

The benefits in reaction control are thought to arise from a number of features.

The small width of the reactor means that reacting species diffuse over much shorter distances before they finally react with other reagents than in conventional reactors. This is particularly important for diffusion limited reactions.

The reacting medium has a high surface area to volume ratio which is thought to allow very efficient heat dissipation to the walls of the reactor in the case of exothermic reactions, thereby reducing the tendency of side products to form. Conversely, the high surface area to volume ratio also allows efficient transfer of heat into the reacting medium from external sources, such as may be required for example in endothermic reactions, or in reaction initiation. Thus the microreactors provide an efficient means for heat sinking from or heat sourcing to the fluid reacting region. The high surface area to volume ratio also provides for a high interfacial area for chemical transfer compared with the volume of fluid to be reacted. Furthermore, it may be possible to use substantially reduced amounts of heat dissipating solvents compared with the amounts used in conventional methods.

The use of flow paths with widths ranging from 10 to 10000 micrometers allows very accurate control over very low flow rates. This fine control over flow rate together with precise control over residence time in the reactor provides a highly controllable reacting system. For example, the residence time in the reactor can be controlled so as to form highly reactive intermediate products in high yield. Such highly reactive intermediates can be difficult to produce under conventional reacting conditions. The intermediate may be used in further reactions and as such may be removed from the reactor, or additionally or alternatively, the reaction may be halted before reaching the final product by quenching it with a heat sink or through other methods such as the use of suitable reagents.

The method of the present invention provides a liquid flow system which has the benefits of laminar flow and no opportunity for aerosol formation, hence eliminating the possibility of explosions. Furthermore, it is possible to construct a temperature gradient along the reactor.

The fine fluidic control of the present method also has the advantage of enabling the matching of the input reagents to the correct stoichiometry of the reaction. This can result in a more efficient and cost-effective process which leaves little or no unreacted reagents which would otherwise reduce the yield of the main product. This also reduces, and may eliminate completely, the need for extensive purification procedures for the product.

As described above the present method is very beneficial for diffusion limited reactions. However, it is also beneficial for kinetically limited reactions.

In addition to the efficient supply of energy such as heat to the reaction region, reaction kinetics may also be enhanced through the careful placement of solid phase catalysts in or near the reaction region. This enhancement is thought to be obtained by virtue of the following two key features. Firstly, the short diffusion distances over which the catalysed reagent must travel before it finally reacts with the other reagents and secondly the large fluid surface area to volume ratios available, enabling the catalyst to be seen by a larger proportion of the fluids. Such diffusion distances are characterised by the expression $Dt/l^2$ where D is the diffusion coefficient, t is the time taken for transport of the catalysed reagent before it reacts with the other reagents and l is the length scale over which diffusion takes place. The optimal range for these catalytic improvements is dependent upon these two characteristics of larger surface to volume ratios and diffusion distance. Clearly the smaller the channel dimension is, the larger the surface to volume ratio will be, leaving $Dt/l^2$ to define the optimal reactor dimension for a given time. For substantial transport (50–100%) of the catalysed reagent, $Dt/l^2$ lies in the range 0.1–1 (see J Crank—The Mathematics of Diffusion—Second Edition—Oxford University Press, 1975). Typical values of D for liquids lie between $10^{-10}$–$10^{-9}$ m$^2$/s which, for transport times of around 1 second, require length scales and thus reactor dimensions normal to the catalyst surface of between 30–100 microns.

The reaction kinetics may also be enhanced by catalytic effects of the reactor walls. This effect is much more marked than with conventional reaction vessels because of the much larger surface area to volume ratio of the microreactor. A catalytic film may be deposited on the reactor walls specifically for this purpose, although in some cases the bare substrate walls may have some catalytic effect. In the case of fluorination reactions, certain reactions seem to involve interactions with the metal fluids formed on the surface of the reactor wall. An increase in reaction yield may be the result.

The start up of reactions may be induced through the use of external influences such as heat, light or electrical activity, as is carried out in conventional chemical synthesis. Additional measures may be used to halt reactions through the use of an external influence or through the removal of an influence. As an example a heater may be used to initiate a reaction and a cooling element to halt the reaction.

The improved reaction control in the present method allows the production of reagents under highly defined conditions. This control will allow hazardous reagents to be produced and controlled such that they are maintained in a safe manner. The reduced inventory of the reagents, both within the lead-in flow paths or microchannels and within the microreactor itself reduces potential risks associated with handling hazardous or explosive reagents.

When large quantities of fluid are required to be reacted, such as in many practical embodiments, a large number of microreactors may be employed. Since large numbers of microreactors may be manufactured relatively cheaply, this provides an efficient way of reacting large quantities of fluid under highly controlled conditions. In addition, in such a "scale-up", the reaction conditions in the microreactors, and hence product distribution, remain unchanged. This is an advantage in comparison to conventional batch reactors where the distribution of products may change as the reaction is scaled up from laboratory-scale to plant-scale.

The present method may be applied to many liquid-liquid, liquid-gas and gas-gas type reactions. Classes of reactions which may benefit from the present method include hydrogenation reactions, oxidation reactions, halogenation reactions, alkylation reactions, acylation reactions, aromatic electrophillic reactions, organometallic reactions and catalytic reactions. It should be noted however that the foregoing list is not exhaustive and the present method may also benefit many other classes of reactions.

The present method has been found to be particularly beneficial for fluorination reactions. Fluorine is a highly reactive poisonous gas. It is used in the production of organofluorine compounds which have a large number of applications, such as in agrochemicals and pharmaceuticals. Fluorination is conventionally carried out in a stirred reactor with the fluorine bubbled in to the solution. The fluorination occurs to yield a range of products due to fluorine's highly reactive nature and the exothermic nature of fluorination reactions. The use of a microreactor according to the present method has advantages over a conventionally sized reactor in allowing an increase in process control through more efficient heat dissipation. This results in increased yield and/or purity in many fluorination reactions. In certain cases, it is possible to use an excess and/or extremely high concentration of fluorine at room temperature.

Figure 2:
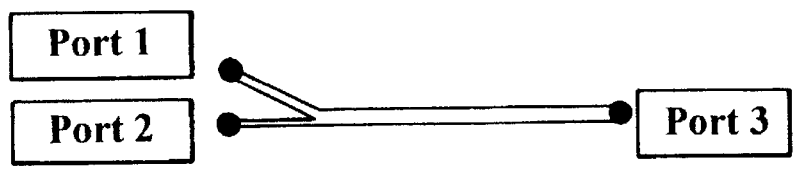
Figure 3:
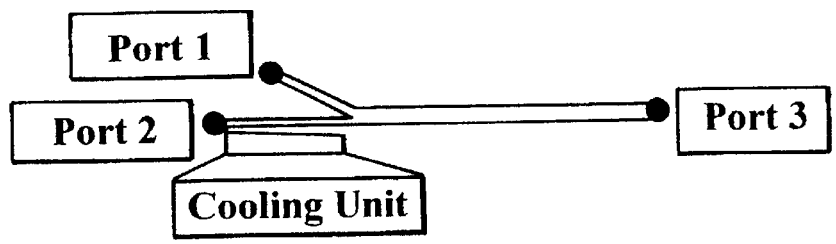

A suitable microreactor for fluorination is shown schematically in FIG. 2. Flow rates of reagents can be controlled such that stoichiometric reaction conditions occur.

The reactor shown in FIG. 2 can be used for a number of reactions. Fluorine gas can be added to the reactor via port 1, with organic compounds being added through port 2. The products are then outputted from port 3. The fluorine gas can also be dissolved in an inert solvent and added through port 1 in a liquid form.

Other examples of reactions which may be carried out and benefit from using the present method include sulphonation of aromatic compounds, chlorination using thionyl chloride, esterification reactions, and acylation reactions.

Figure 4:
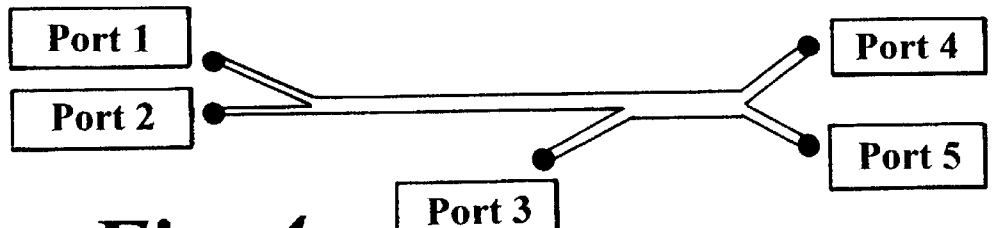

Carboxylic acids could be chlorinated with thionyl chloride, using the system shown in FIG. 2. To wash out the hydrochloric acid produced, a system such as shown in FIG. 4 could be used. The carboxylic acid and thionyl chloride would then be introduced into the system through ports 1 and 2. A wash solution of sodium hydroxide would be added through port 3, with the product, an acyl chloride, being removed through port 4 and the aqueous phase leaving via port 5.

The acid chloride produced as described above could be used for a number of reactions on a microscale including the production of esters through reaction with an alcohol, and acylations of organic compounds. Thionyl chloride may also be reacted with an alcohol directly to yield a chlorinated alkane.

Other reagents of this type could be reacted in a similar manner, such as phosphorous oxychloride with alcohols, which yields phosphate esters. Phosphorus trichloride could be reacted with an alcohol to yield a phosphonate.

Hydrogenation reactions could be carried out in a similar fashion to the above fluorination reactions where an organic liquid could be contacted with a flow of hydrogen gas. Examples of simple systems based on this would be the reduction of nitrobenzene to yield aniline, and the reduction of a nitrile to yield an amine. Oxidations with oxygen could also be carried out in a similar process, for example the oxidation of toluenealdehyde to yield phthalic acid.

Fluidic organometallic reagents such as Grignard reagents may be used in microreactors according to the present method, when the Grignard reagent has been prepared for the reaction. Reagents to quench the reactions, such as water, can be introduced using a system as shown in FIG. 4.

Figure 5:
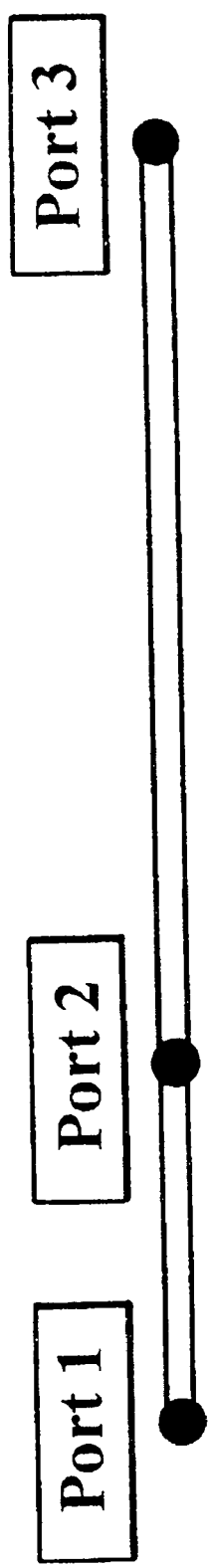

FIG. 5 shows an alternative arrangement to that of FIG. 2, being useful for a range of reactions, including fluorination reactions. In this case the region of contact between the fluids includes essentially the whole of the flow path of one of the fluids. The arrangement is such that the fluid introduced via Part 2 does not form a stratified layer as in the case of the FIG. 2 embodiment, but contacts and intimately mixes with the reagent introduced via Part 1. The arrangement may be such that one fluid passes down the walls of the channel to Part 3, whilst the other fluid is maintained at the centre of that channel.

Reactors such as those illustrated in FIGS. 1 to 4 may be made of, for instance, nickel. In typical embodiments, the channel was 0.5 mm wide and 40 mm long. The reactor was operated at room temperature and in some cases a heated nickel tube was added to the outlet port, the tube having an internal diameter of 0.5 mm and a length of 500 mm.

In the case of fluorination reactions, the reactor can be made from any substance resistant to fluorine gas, such as polytetrafluoroethylene (PTFE), polychlorotrifluoroethylene (PCTFE) or perfluoroalkoxy polymer (PFA), or any substance which can be rendered passive to fluorine gas, usually by forming a metal fluoride surface layer such as nickel, copper, aluminium or alloys such as monel and stainless steel. The inside diameter of the reactor channel will generally, but not exclusively, be between 1.0 mm and 0.05 mm, preferably between 0.75 mm and 0.1 mm, especially between 0.5 mm and 0.2 mm. The reactor channel length will generally be between 200 mm and 10 mm, preferably between 150 mm and 20 mm, most preferably between 100 mm and 40 mm. The ratio of tube length to inside diameter will generally be between 1000:1 and 2:1 and preferably be between 200:1 and 80:1. The reactor will generally be operated between 250° C. and −80° C., preferably between 25° C. and −10° C.

The reactor may be extended by the addition of tubing to the outlet port. The tubing can be made from any substance resistant to fluorine gas, such as polytetrafluoroethylene (PTFE), fluorinated ethylene polymer (FEP) or perfluoroalkoxy polymer (PFA), or any substance which can be rendered passive to fluorine gas, usually be forming a metal fluoride surface layer such as nickel, copper, aluminium or alloys such as monel and stainless steel. The inside diameter of the tubing will generally be similar to that of the reactor. The tube length will generally be between 0.5 m and 10 m, preferably between 0.1 m and 1 m, most preferably between 0.1 m and 0.5 m. The tubing may be operated at temperatures between −80° C. and 250° C., more preferably between 100° C. and 200° C.

Embodiments of the invention will now be described in detail by way of the following examples only.

EXAMPLE 1

Cyclohexane,1,1,2,2,3,3,4,4,5,5,6,-undecafluoro-6-[1,2,2,3,3,3-hexafluoro-1-(trifluoromethyl)propane has been prepared by the present method. The reaction scheme is shown in equation 1 of FIG. 6. Cyclohexane-6-[1,1,1-trifluoro-1-(trifluoromethyl)-propene] was reacted with a solution of fluorine dissolved in flutec. The reaction yielded a large proportion of perfluorinated material, including fluorination at the tertiary carbon of the cyclohexyl, a difficult position to fluorinate under conventional conditions.

EXAMPLE 2

Figure 6:
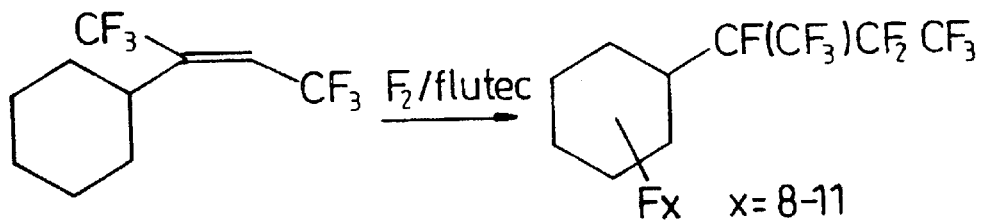
FIG. 6 depicts chemical reactions of difference chemical compounds being reacted with fluorine gas.
Figure 6:
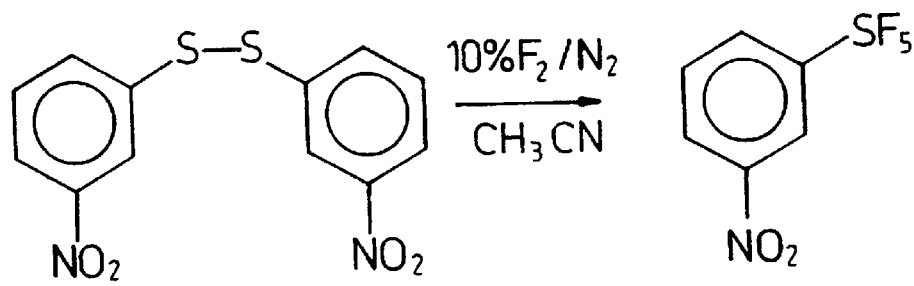
Figure 6:
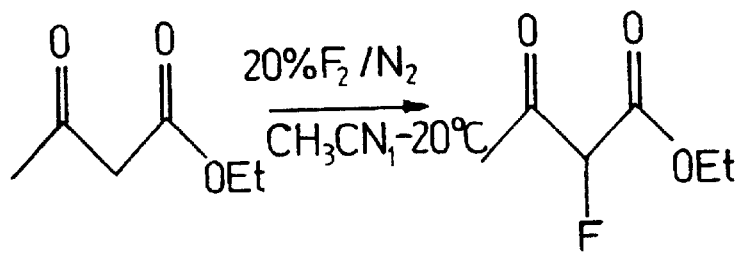

Sulfur pentafluoro-3-nitrobenzene was produced in a microreactor as in FIG. 2 using a solution of bis(3-nitrophenylsulphide) in acetonitrile which was reacted with 10% fluorine gas in nitrogen, as shown in equation 2 of FIG. 6. The yield of the product was 75%, with a large conversion of fluorine. Conventional macroscale synthesis of the product has yields in the order of 38%.

EXAMPLE 3

Ethyl acetoacetate was reacted with fluorine gas to yield the compound, ethyl 2-fluoroacetoacetate, shown in equation 3 of FIG. 6. The acetoacetate was dissolved in acetonitrile, which was subsequently cooled to −20° C. prior to mixing in the microreactor tube as shown schematically in FIG. 3. Yields of >80% were observed with conversions of fluorine of up to 90%. In comparison, macroscale reactions produced yields of 60–80%, with low conversion of the fluorine.

EXAMPLE 4

Figure 7:
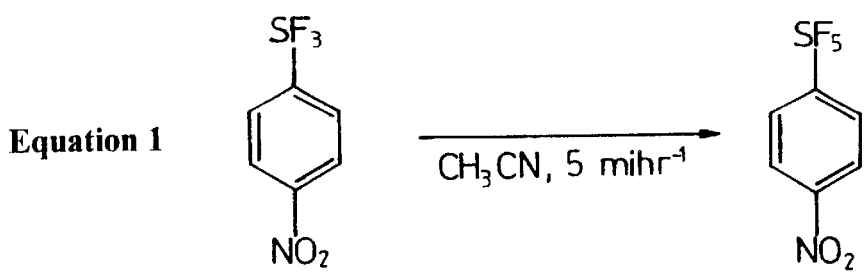
FIG. 7 depicts chemical reactions of different chemical compounds being reacted with fluorine gas, together with the rates of injection of the compounds into the microreactors.
Figure 7:
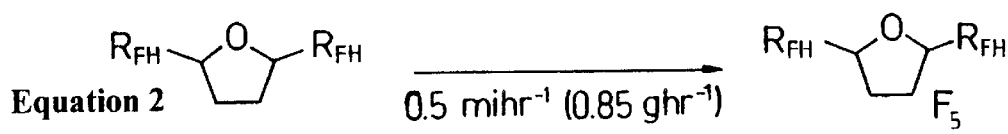
Figure 7:
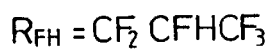
Figure 7:
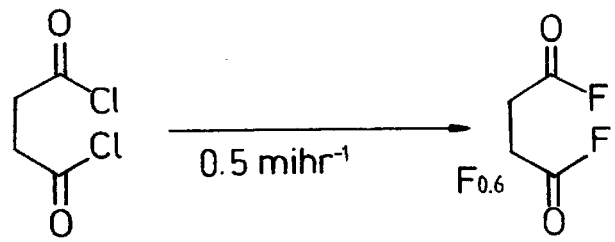
Figure 7:
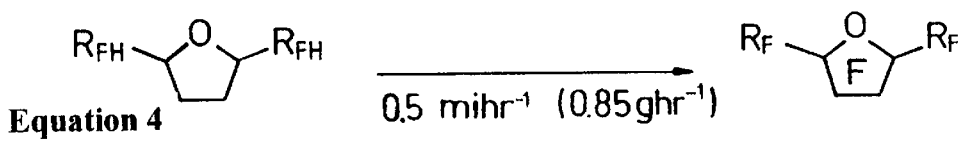
Figure 7:
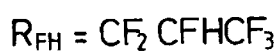
Figure 7:
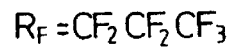
Figure 7:
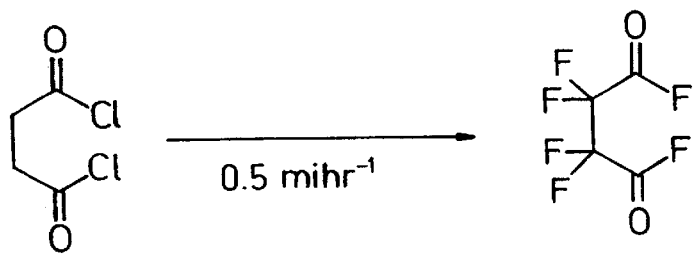

A solution of 4-nitrophenylsulphur trifluoride (1.4 g, 6.5 mmol) in dry acetonitrile (14 ml) was fed into the microreactor, at a rate of 5 mlhr$^{-1}$ at room temperature. Simultaneously, a flow of 10% fluorine was set up through the micro-reactor at a rate of 10 mlmin$^{-1}$. The liquid products were shaken with sodium fluoride to remove any remaining HF, then rotorvapped to remove the majority of acetonitrile, washed with water, extracted with dichloromethane, dried over magnesium sulphate and excess solvent was removed on the rotorvapor. Analysis by NRM spectroscopy identified a 44% conversion of the trifluorosulphur compound to give 4-nitrophenyl sulphur pentafluoride according to equation 1 of FIG. 7; $\delta_F$ +61.2 ppm (d, J 145 Hz, SF, 4F), +80.5 ppm (quintet, J 145 Hz, SF, 1F); M+249.

EXAMPLE 5

2,5-Bis(2H-hexafluoropropyl)tetrahydrofaran (6.8 g, 18 mmol) was injected at a rate of 0.5 mlhr$^{-1}$ (0.85 ghr$^{-1}$) into the micro-reactor, at room temperature, with a simultaneous gas flow of 50% fluorine in nitrogen at a rate of 15 mlmin$^{-1}$ (8-fold excess). The reaction (equation 2 of FIG. 7) was terminated after sixteen hours and approximately 8 mls of colourless product were recovered. The products were washed with water and dried over magnesium sulphate. Analysis by gas chromotography-mass spectroscopy and NMR spectroscopy identified complete conversion of starting material to a mixture of geometric and stereo-isomers cotaining tetrafluoro-2,5-bis(2H-hexafluoropropyl) tetrahydrofuran (M$^+$−19, 425), pentafluoro-2,5-bis(2H-hexafluoropropyl)atetrahydrofuran (M$^+$−19, 443) and hexafluoro-2,5-bis(2H-hexafluoropropyl)tetrahydrofuran (M$^+$−19, 461); $\delta_F$ −75.8, −82.6 ppm (m, CF$_3$), −126.7 ppm (overlapping m, $CF_2$), −213.7 ppm (overlapping m, CH); $\delta_H$ 2.73 ppm (overlapping m, $CH_2$), 5.05 ppm (overlapping m, CFH).

EXAMPLE 6

Succinyl chloride (2.8 g, 18 mmol) was injected at a rate of 0.5 mlhr$^{-1}$ (0.7 ghr$^{-1}$) with a simultaneous gas flow of 50% fluorine in nitrogen, at a rate of 15 mlmin$^{-1}$ (8-fold excess), into the micro-reactor, at room temperature, and then through a heated nickel tube, at 80° C. The reaction was terminated after four hours and approximately 2 mls of light yellow liquid product were recovered (equation 3 of FIG. 7). The products were shaken with sodium fluoride, to remove HF, and analysed by NMR spectroscopy which identified almost complete conversion of starting material to a mixture of polyfluuorinated products; $\delta_F$ +40 ppm (s, O=CF), −102 & −108 ppm (m, $CF_2$), −179.8 & −193.3 ppm (m, CFH); $\delta_H$ 3.0 & 3.5 ppm (m, $CH_2$), 5.5 ppm (m, CFH).

EXAMPLE 7

2,5-Bis(2H-hexafluoropropyl)tetrahydrofuran (6.8 g, 18 mmol) was injected at a rate of 0.5 mlhr$^{-1}$ (0.85 ghr$^{-1}$) into the micro-reactor, at 0° and then through a heated nickel tube (180° C.), with a simultaneous gas flow of 50% fluorine in nitrogen at a rate of 20 mlmin$^{-1}$ (10-fold excess). The reaction (equation 4 of FIG. 7) was terminated after sixteen hours and approximately 8 mls of colourless product were recovered. The products were washed with water and dried over magnesium sulphate. Analysis by gas chromotography-mass spectroscopy and NMR spectroscopy identified complete conversion of starting material to a mixture of cis and trans isomers of perfluoro-2,5-dipropyltetrahydrofuran.

EXAMPLE 8

Succinyl chloride (2.8 g, 18 mmol) was injected at a rate of 0.5 mlhr$^{-1}$ (0.7 ghr$^{-1}$) with a simultaneous gas flow of 50% fluorine in nitrogen, at a rate of 15 mlmin$^{-1}$ (8-fold excess), into the micro-reactor, at room temperature, and then through a heated nickel tube, at 180° C. The reaction (equation 5 of FIG. 7) was terminated after four hours and approximately 2 mls of colourless liquid product were recovered. The products were shaken with sodium fluoride, to remove HF, and analysed by NMR spectroscopy which identified complete conversion of starting material to perfluorosuccinyl fluoride.

What is claimed is:

1. A method of carrying out a reaction between at least two miscible fluids, one of the at least two miscible fluids comprising a compound to be fluorinated and another of the at least two fluids comprising a fluorinating agent, the method comprising providing respective flow paths for the at least two miscible fluids, said flow paths communicating with each other, and flowing the at least two miscible fluids along said flow paths such that in said region the at least two miscible fluids contact each other and a chemical reaction between said at least two miscible fluids occurs, said region having a width perpendicular to the direction of flow in the range of 10–10,000 micrometers.

2. A method according to claim 1 and wherein the width is in the range 10–500 micrometers.

3. A method according to claim 2 and wherein the width is in the range 10–200 micrometers.

4. A method of carrying out a fluorination reaction, as in claim 1 and wherein the at least two miscible fluids are each independently a liquid, a gas, or a supercritical fluid.

5. A method according to claim 1 and wherein energy is supplied to said region from an external source.

6. A method according to claim 5 and wherein the energy is at least one of heat, light and electrical energy.

7. A method according to claim 5 and wherein the energy is supplied to initiate the reaction.

8. A method according to claim 1 and wherein cooling is applied to said region.

9. A method according to claim 1 and wherein the reaction is quenched before it reaches completion and an intermediate product is isolated.

10. A method according to claim 1 and wherein a solid catalyst is located at or near said region.

11. A method according to claim 1 and wherein at least one of the least two miscible fluids is hazardous or explosive.

12. A method according to claim 1 and wherein the fluorinating agent is fluorine gas.

13. A method according to claim 1 wherein said region includes essentially the whole or the flow paths of one of the fluids.

14. A method according to claim 13 wherein the arrangement is such that in said region one of said fluids substantially surrounds the or another of said fluids transversely to the direction of fluid flow.

15. A method according to claim 1 wherein said region has a width between 0.75 mm and 0.1 mm.

16. A method according to claim 15 wherein said width is between 0.5 mm and 0.2 mm.

17. A method according to claim 1 wherein said region has a length between 150 mm and 20 mm.

18. A method according to claim 17 wherein said length is between 100 mm and 40 mm.

19. A method according to claim 18 wherein the ratio of length to width of said region is between 200 and 80.

20. A method according to claim 1 wherein the temperature in said region is from 25° C. to −10° C.

21. A method according to claim 1 wherein the fluids are fed from said region into tubing having a length between 0.05 m and 120 m.

22. A method according to claim 21 when said tubing has a length between 0.1 m and 0.5 m.

23. A method according to claim 21 wherein the temperature within said tubing is maintained between 100° C. and 200° C.

24. A method of carrying out a fluorination reaction between at least two fluids that are miscible, and wherein a multiplicity of flow paths as in claim 1 are employed thereby forming a multiplicity of regions in which the chemical reaction occurs.

* * * * *